United States Patent [19]
Brockbank et al.

[11] Patent Number: 5,110,722
[45] Date of Patent: May 5, 1992

[54] CELL, TISSUE OR ORGAN STORAGE SOLUTION

[75] Inventors: Kelvin G. M. Brockbank, Marietta, Ga.; Katherine A. Anderegg, Pittsburgh, Pa.

[73] Assignee: CryoLife, Inc., Marietta, Ga.

[21] Appl. No.: 433,952

[22] Filed: Nov. 9, 1989

[51] Int. Cl.$^5$ .......................... A01N 1/02; C12N 5/06
[52] U.S. Cl. .............................................. 435/1; 435/2; 435/240.1; 435/240.2; 435/240.25; 435/240.3; 435/240.31
[58] Field of Search ...................... 435/1, 240.1, 240.2, 435/2, 240.25, 240.3

[56] References Cited

U.S. PATENT DOCUMENTS

| | | |
|---|---|---|
| Re. 30,985 | 6/1982 | Cartaya . |
| 4,186,253 | 1/1980 | Yokoyama et al. . |
| 4,443,546 | 4/1984 | Stemerman et al. . |
| 4,533,637 | 8/1985 | Yamane et al. . |
| 4,554,251 | 11/1985 | Hink, Jr. . |
| 4,560,655 | 12/1985 | Baker . |
| 4,608,341 | 8/1986 | Ambesi-Impiombato . |
| 4,681,839 | 7/1987 | Swartz . |
| 4,757,018 | 7/1988 | Brown . |

OTHER PUBLICATIONS

Mohamed et al–Chemical Abstracts vol. 99 (1983) p. 101924d.
Carney et al–Chemical Abstracts vol. 101 (1984) p. 207,173h.
Mather et al–Chem, Abstracts, vol. 96 (1982) p. 98402n.
Mohamed et al–In Vitro vol. 19 (1983) pp. 471–478.
Hoffman et al, "Combined Cold Storage-Perfusion Preservation With A New Synthetic Perfusate", Transplantation, vol. 47, 32–37, No. 1, No. 1, Jan. 1989 pp. 32–37.
Karow, ed. *Organ Preservation for Transplantation*, Marcel Dekker, Inc., N.Y. WO 665 K185o 1981 pp. 533–575.

*Primary Examiner*—Sam Rosen
*Attorney, Agent, or Firm*—Cushman, Darby & Cushman

[57] ABSTRACT

The present invention relates to a method of maintaining viability of a cell, tissue or organ. The method involves maintaining the cell, tissue or organ in contact with a storage solution comprising transferrin and selenium at a subambient temperature in a non-frozen state. The invention further relates to a storage solution suitable for use in the above-described method. In one embodiment, the solution comprises insulin, transferrin, hydrocortisone, selenium and 4-(2-hydroxyethyl)-1-piperazineethanesulfonic acid.

14 Claims, 3 Drawing Sheets

CELL, TISSUE OR ORGAN STORAGE SOLUTION

BACKGROUND OF THE INVENTION

Technical Field

The present invention relates in general, to the preservation of organs, tissues and cells during storage and transport and, in particular, to a method of maintaining organs, tissues and cells in a viable state prior to transplantation, and to a composition suitable for use in such a method.

Background Information

Ischemia, a localized tissue hypoxia resulting from partial or complete loss of blood circulation, ensues rapidly upon death of an organism. In designing a protocol for storing a tissue prior to transplantation, the susceptibility of the particular tissue to ischemia must be considered. One factor that influences the rate at which ischemia produces cellular injury, and subsequently cell death, is temperature. Kidneys, for example must be procured immediately after cessation of donor heartbeat, and can be stored for only 1-3 days at 0°-4° C., using current technology. The exact time is dependant upon whether or not continuous perfusion is employed. This is in contrast with bone marrow, which can tolerate at least 12 hours of warm ischemia post mortem and 3 days of cold ischemia at 0°-4° C.

In order to extend the period for which particular cells, tissues and organs can be maintained in a state which will permit subsequent successful transplantation into a recipient host, new methods must be developed. One such method is provided by the present invention.

SUMMARY OF THE INVENTION

It is a general object of the invention to provide a method of maintaining cells, tissues and organs in a viable state.

It is a specific object of the invention to provide a method of storing cells, tissues and organs at refrigerated temperatures prior to transplantation.

It is another object of the present invention to provide a tissue storage solution that permits storage of cells, tissues and organs at refrigerated temperatures for periods of time longer than is possible using present clinically accepted solutions.

Further objects and advantages of the present invention will be clear from a reading of the description that follows.

The present invention relates to a method of delaying the detrimental effects of ischemia on organ, tissue and cell viability, and to a storage solution suitable for use in such a method.

In one embodiment, the present invention relates to a method of storage comprising the steps of:

i) contacting a cell, tissue or organ to be stored with a solution comprising transferrin and selenium; and ii) maintaining the cell, tissue or organ in contact with the solution at a sub-ambient temperature in a non-frozen state.

In another embodiment, the present invention relates to a storage solution comprising insulin, transferrin, hydrocortisone, selenium and a Goodes buffer, for example, 4-(2-hydroxyethyl)-1-piperazineethanesulfonic acid (HEPES).

DETAILED DESCRIPTION OF THE INVENTION

Figure 1:
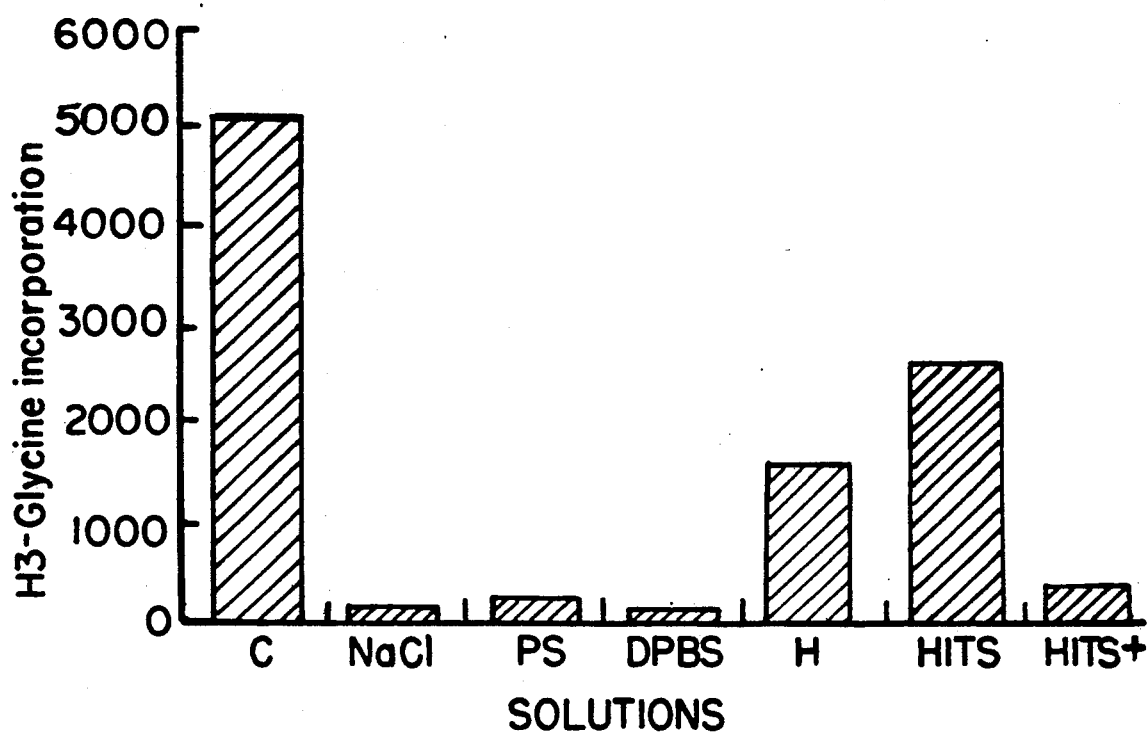
FIG. 1: Comparison of six cold storage solutions using canine anterior cruciate ligament-derived fibroblasts in vitro.

The present invention relates to a method of storing cells, tissues and organs, and to a storage solution suitable for use in such a method. The present storage method is such that viability of the material is maintained. Maintenance of viability permits subsequent successful transplantation of the stored material into a recipient host.

In the present method, material to be stored is placed in contact with a storage solution comprising transferrin and selenium, advantageously at concentrations in the ranges of 2.5 $\mu$g/ml to 10 $\mu$g/ml and 2.5 ng/ml to 7.5 ng/ml, respectively. In a preferred embodiment, insulin and hydrocortisone are also present in the storage solution, advantageously at concentrations in the ranges of 2.5 $\mu$g/ml to 7.5 $\mu$g/ml and 25 ng/ml to 40 ng/ml, respectively. In a most preferred embodiment, a Goodes buffer, for example HEPES, is also present in the solution at a concentration in the range of 10 mM to 30 mM (corresponding to 2.92-8.85 g/l in the case of HEPES). The inclusion of a Goodes buffer in the storage solution is particularly advantageous where storage for more than two days is required. For shorter storage periods, other pharmaceutically acceptable buffers, for example, a bicarbonate buffer, can be used.

The above-described components of the tissue storage solution of the present invention can be present, for example, in a medium capable of supporting cellular metabolism in vitro at 37° C. or the components can be present in a buffered physiological salt solution that is incapable of supporting cellular metabolism at 37° C. Such salt solutions can include a carbohydrate source (for example, glucose).

In the present method, cell viability is maintained by storing the cells, tissues or organs in the above-described solution at sub-ambient temperatures, in a non-frozen state. Advantageously, temperatures in the range of −4° to 4° C. are used.

Materials suitable for storage according to the present method include, but are not limited to, heart, kidney, lung, liver, cornea, pancreas, skin, blood vessels, tendons, ligaments, bone, bone marrow, endocrine and exocrine glands, gametes, ova, nerves, gastrointestinal tract, ureter, bladder, or structures or cellular components derived from any of the above. Where intact organs are to be stored, such organs are flushed with the above-described solution prior to storage.

The following non-limiting Examples further describe the present invention.

EXAMPLE 1

Comparison of Six Storage Solutions

Confluent cultures of canine anterior cruciate ligament(ACL)-derived fibroblasts were placed, for five days at 0°-4° C., in: physiological saline (0.9% (w/v)

NaCl) (designated NaCl); 2) a culture medium containing fetal calf serum (Dulbecco's Modified Eagle Medium plus 10% v/v fetal calf serum) (designated PS); 3) a buffered physiological salt solution (0.10 g/l $CaCl_2$ (anhydrous), 0.20 g/l KCl, 0.20 g/l $KH_2PO_4$, 0.10 g/l $MgCl_2.6H_2O$, 8.00 g/l NaCl, and 2.16 g/l $Na_2HPO_4.H_2O$) (designated DPBS); 4) Hanks Balanced Salt Solution as in Table I without hydrocortisone, insulin, transferrin and selenium and containing 15 mM HEPES instead of 25 mM (designated H); 5) the solution of Table I (designated HITS); or 6) the solution of Table I plus chondroitin sulfate (25 g/l) and sucrose (47.922 g/l) (designated HITS.).

At the end of this period, the solutions were removed from the cultures, the cells were washed, and placed in contact with fresh serum-free culture medium. After 2 hrs. of incubation in the serum-free medium, the cells were labeled with tritiated glycine at 37° C. in a 5% $CO_2$ and air incubator using a technique adopted from that detailed below in Example 2. The relative protein incorporation between the experimental groups is an indication of the level of cellular viability.

TABLE I

|  | g/l |
| --- | --- |
| $CaCl_2$ (anhydrous) | 0.14 |
| KCl | 0.40 |
| $KH_2PO_4$ | 0.06 |
| $MgCl_2.6H_2O$ | 0.10 |
| $MgSO_4.7H_2O$ | 0.10 |
| NaCl | 8.00 |
| $NaHCO_3$ | 0.35 |
| $Na_2HPO_4.7H_2O$ | 0.09 |
| D-Glucose | 1.00 |
| Phenol Red | 0.01 |
| Hepes | 4.425 |
| Transferrin | 0.005 |
| Insulin | 0.005 |
| Selenium | 0.000005 |
| Hydrocortisone | 0.000036 |

The results shown in FIG. 1 clearly indicate the superiority of the solution of the present invention (that given in Table I) over the others tested. (C=control—no storage at 0°-4° C.; storage medium=Dulbecco's Modified Eagle Medium plus 10% v/v fetal calf serum.

EXAMPLE 2

Comparison of Hydrocortisone, Insulin, Transferrin and Selenium-Containing Storage Solution and Euro-Collins Storage Solution Bisected human heart valve leaflets were placed in either the solution described in Table I or Euro-Collins solution at 4° C. for 1-5 days. (Euro-Collins=$KH_2PO_4$ (2.05 g/l), $KHPO_4$ (7.40 g/l), KCl (1.12 g/l), $NaCO_3$ (0.84 g/l), and glucose (38.5 g/l).) After cold storage, the leaflets were washed and placed in tritiated glycine and incorporation of the isotope into protein was determine after 48 hrs of incubation using the following protocol:

Tritiated Labelling of Tissue

Day 1—Make up a 16 µCi/ml H-glycine solution in serum free Dulbecco's Modified Eagle Medium (DMEM). Cut tissue up into small pieces and place in a 5 ml snap-cap tube. Add 0.5 ml of the H-glycine to each tube. Incubate for 48 hours at 37° C.

Day 2 - Decant medium from the tubes and wash tissue quickly twice with phosphate buffered saline (PBS). Add PBS and let sit for 30 minutes. Remove PBS and add more PBS. Incubate overnight at 4° C.

Day 3—Decant PBS off of tissue and place tissue into 15×100 mm glass tubes. Wash for 15 minutes in alcohol, then wash for 15 minutes with ether. Remove ether and allow the tissue to dry for at least one hour. Weigh and record weight of tissue from each tube. Place all tissue into clean 12×75 mm glass tubes.

Add 200 µl $H_2O$ to each tube and let rehydrate for 30 minutes to 1 hour.

Add 500 µl 1M NaOH to each tube and place tubes in a heating block at 60° C. Allow 60 minutes incubation for valve tissue.

Pipette samples into microtubes and sonicate twice for 20 seconds each time Centrifuge in microfuge for 2 minutes.

Apply 100 µl of each sample to glass fiber filter discs. Allow to dry for at least one hour. Move filter discs to glass scintillation vials and add 2 ml ice cold 10% trichloroacetic acid (TCA) to each vial. Refrigerate for 30 minutes minimum. Remove TCA and wash four times with 3 ml ice cold alcohol. Then wash twice with 3 ml ice cold ether. Allow filter discs to dry for at least one hour. Add 130 µl $H_2O$ to each filter disc. Add 1 ml Protosol to each vial. Vortex vigorously. Add 10 ml scintillation fluid and 100 µl glacial acetic acid. Transfer vials into racks, place racks in counter and allow to dark adapt for 30 minutes before counting. Count each vial for 5 minutes.

Figure 2:
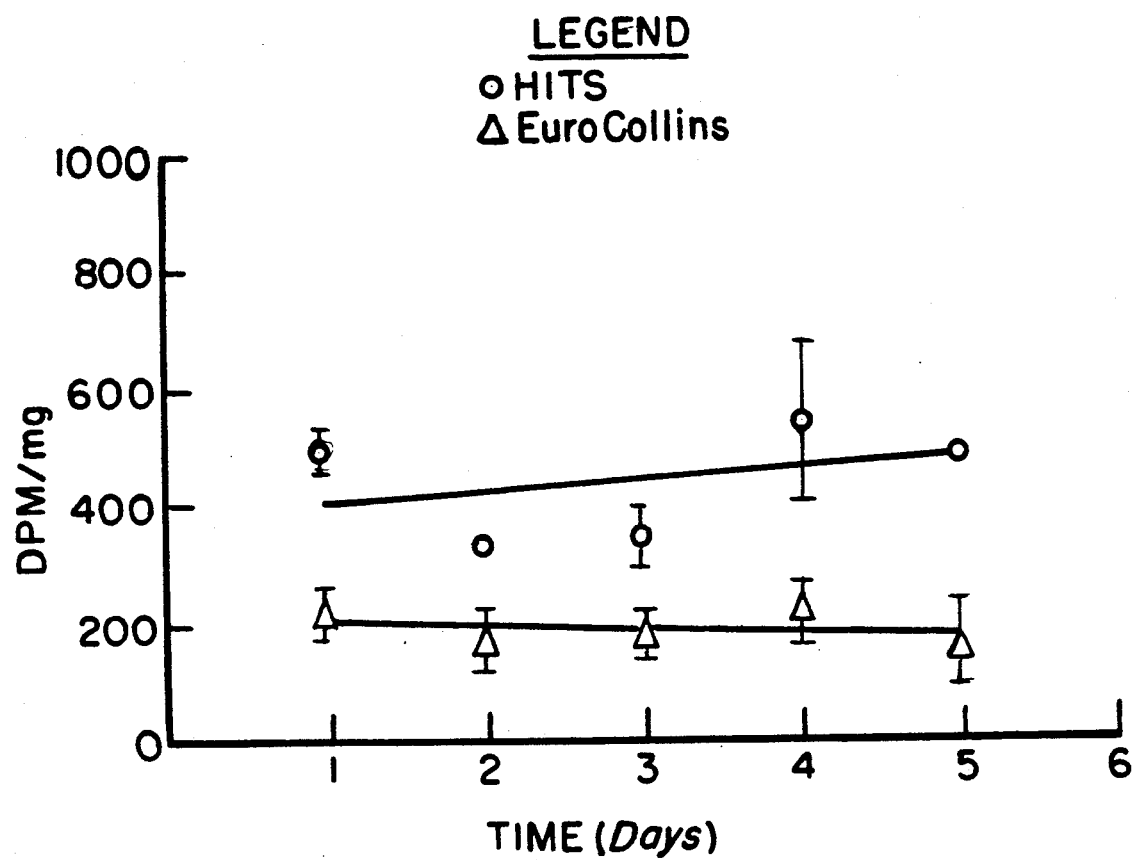
FIG. 2: Cold ischemia study using hydrocortisone, insulin, transferrin and selenium-containing storage solution and Euro-Collins storage solution.

The results are summarized in FIG. 2. A total of 27 comparisons were done after 1-5 days of incubation. In 23 out of the 27 comparisons, the solution described in Table I was clearly superior. In only one instance did the Euro-Collins solution support protein synthesis levels greater than the solution described in Table I. In three cases, the numbers were similar.

These results demonstrate a highly significant maintenance of cellular viability by the storage solution of the present invention, relative to the current clinically accepted alternative.

EXAMPLE 3

Effects of Removal of Hydrocortisone, Insulin, Transferrin and Selenium on Cell Storage at 4° C.

Human kidney-derived proximal tubule cells were plated on bovine type I collagen/fetal calf serum-coated Costar 24 well plates and placed in either complete solution (C) (see Table II) or in the solution shown in Table I from which either one or all of the following had been removed: hydrocortisone (H), insulin (I), transferrin (T), or selenium (S). The plates were then placed in a refrigerator at 4° C. for 72 hours. Viability was assayed by the neutral red spectrophotometric assay described below in Example 4.

TABLE II

| Complex culture medium used for testing HITS components. | | | |
| --- | --- | --- | --- |
| COMPONENTS | mg/L | | |
| INORGANIC SALTS: | | Vitamins | |
| $CaCl_2$(anhyd.) | 100 | Biotin | 0.00365 |
| $CaCl_2.2H_2O$ | 22 | D-Capantothenate | 2.24 |
| $CuSO_4.5H_2O$ | 0.001245 | Choline chloride | 8.98 |
| $FeSO_4.7H_2O$ | 0.417 | Folic acid | 2.65 |
| KCl | 311.8 | i-Inositol | 12.60 |
| $MgCl_2.6H_2O$ | 61 | Niacinamide | 2.0185 |
| $MgSO_4.7H_2O$ | 100 | Pyridoxine HCl | 0.031 |
| NaCl | 6999.5 | Riboflavin | 0.219 |
| $NaHCO_3$ | 2438 | Thiamine HCl | 2.17 |
| $Na_2HPO_4.7H_2O$ | 134 | Vitamin $B_{12}$ | 0.68 |

TABLE II-continued

Complex culture medium used for testing HITS components.

| COMPONENTS | mg/L | | |
|---|---|---|---|
| $ZnSO_4 \cdot 7H_2O$ | 0.4315 | Pyridoxal HCl | 2.0 |
| $Fe(NO_3)_3 \cdot 9H_2O$ | 0.05 | | |
| $NaH_2PO_4 \cdot H_2O$ | 62.5 | | |
| OTHER COMPONENTS | | | |
| D-Glucose | 1401 | | |
| Hypoxanthine | 2.05 | | |
| Linoleic acid | 0.042 | | |
| Lipoic acid | 0.105 | | |
| Phenol red | 8.1 | | |
| Putrescine 2HCl | 0.0805 | | |
| Sodium pyruvate | 110 | | |
| Thymidine | 0.365 | | |
| AMINO ACIDS: | | | |
| L-Alanine | 4.45 | | |
| L-Arginine HCl | 147.5 | | |
| L-Asparagine.$H_2O$ | 7.505 | | |
| L-Aspartic acid | 6.65 | | |
| L-Cysteine | 24 | | |
| L-Cysteine HCl.$H_2O$ | 17.56 | | |
| L-Glutamic acid | 7.35 | | |
| L-Glutamine | 365 | | |
| Glycine | 18.75 | | |
| L-Histidine HCl.$H_2O$ | 31.48 | | |
| L-Isoleucine | 54.47 | | |
| L-Leucine | 59.05 | | |
| L-Lysine HCl | 91.25 | | |
| L-Methionine | 17.24 | | |
| L-Phenylalanine | 35.48 | | |
| L-Proline | 17.25 | | |
| L-Serine | 26.25 | | |
| L-Threonine | 53.45 | | |
| L-Tryptophan | 9.02 | | |
| L-Tyrosine | 38.70 | | |
| L-Tyrosine(disodium salt) | — | | |
| L-Valine | 52.85 | | |

Figure 3:
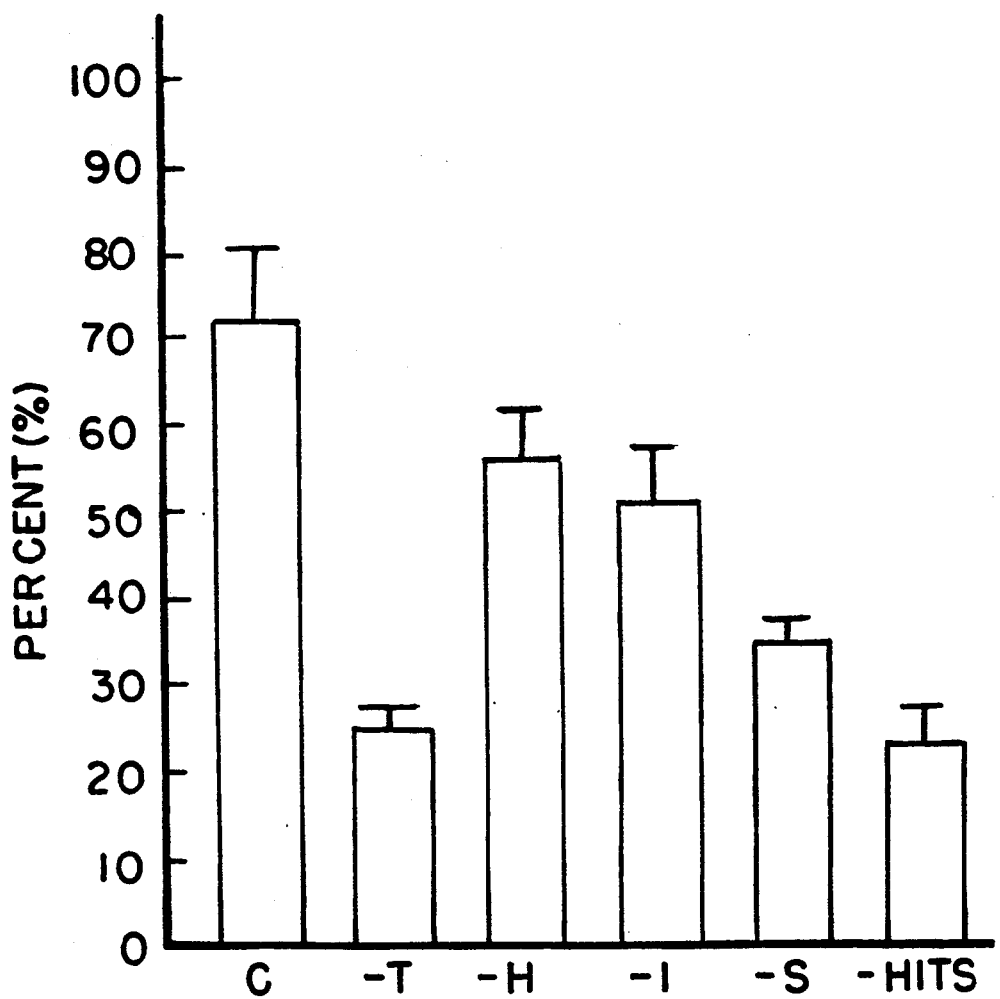
FIG. 3: Effects of hydrocortisone, insulin, transferrin and selenium removal on cell survival at 4° C.

Data shown in FIG. 3 are expressed as the mean survival ±1 S.E. of 4–6 experiments in percent of 37° C. controls.

EXAMPLE 4

Influence of Divalent Cations ($Ca^{+2}$ and $Mg^{+3}$) on Cell Viability in the Presence of HEPES and Bicarbonate Buffers.

In order to access the effects of HEPES and bicarbonate buffers on the viability of cells stored in the absence of divalent cations, human proximal tubule cells were plated on bovine type 1 collagen/fetal calf serum coated Costar 24 well plates and placed in the solutions indicated below in Table III (which solutions are based on that shown in Table I) for 24, 48, or 72 hours under cold (4° C.) ischemic conditions. N=4 for each solution in each of the four experiments performed. All data is expressed in Table III as a percent survival compared to a 37° C. control as assessed by the neutral red spectrophotometric assay described as follows:

Neutral Red Assay

Highest quality Neutral Red dye was obtained from Aldrich Chemical Co. (Milwaukee, Wis.). A 0.5% solution was prepared in tris-buffered saline (TBS). A ten fold concentrated TBS stock was prepared as follows: to 1.0 liter of distilled deionized water was added 24.2 g Trizma 7.7 (Sigma Chemical Co., St. Louis, Mo.), 68.0 g NaCl, 2.0 g KCl, 2.0 g $MgCl_2 \cdot 6H_2O$, and 1.0 g $CaCl_2$ (anhydrous). The saline was then filter sterilized using a 0.22 μ nitrocellulose filter. The saline stock was diluted to 1 X using distilled deionized water. To prepare the Neutral Red solution, 0.5g Neutral Red was added to 100 ml 1X TBS solution, care being taken to minimize the light exposure of this photosensitive dye. The dye solution was filtered using Whatman No. 42 paper just prior to use.

Kidney tubule cells were gently washed 4X with TBS which had been warmed to 37° C. Following suction removal of the last saline wash. 0.5 ml of 0.5% Neutral Red in TBS warmed to 37° C. was added to each well. The plates were then floated in a covered 37° C. water bath for 30 min to allow maximum dye uptake. The unabsorbed Neutral Red solution was then aspirated off and the cells were washed 4X with cold TBS at 4° C. The dye was extracted with cold 50% ethanol at 4° C. for 15 min. A 0.15 ml aliquot was then drawn from each well and placed in the wells of Costar 96-well flat-bottom plates. Controls consisted of 50% ethanol blanks and 1X TBS blanks. Samples were read using a 450 nm filter on a Titertek Multiskan ELISA plate reader. Three rows of serial dye dilutions in 50% ethanol were used to generate a concentration curve.

TABLE III

| BUFFER | CATIONS | DAY 1 | DAY 2 | DAY 3 |
|---|---|---|---|---|
| HEPES | Ca, Mg | 74% | 61% | 41% |
| HEPES | Ca | 98% | 93% | 80% |
| HEPES | Mg | 76% | 60% | 44% |
| HEPES | NONE | 100% | 97% | 88% |
| $HCO_3^-$ | Ca, Mg | 79% | 65% | 45% |
| $HCO_3^-$ | Ca | 97% | 89% | 52% |
| $HCO_3^-$ | Mg | 80% | 64% | 48% |
| $HCO_3^-$ | NONE | 99% | 92% | 59% |

$Ca^{2+}$ = $CaCl_2$ (anhydrous) (0.14 g/l)
$Mg^{2+}$ = $MgCl_2 \cdot 6H_2O$ [0.10 g/l] and $MgSO_4 \cdot 7H_2O$ [0.10 g/l]
HEPES = 5.66 g/l (20 mM)
$HCO_3^-$ = $NaHCO_3$ [0.35 g/l]

These results clearly demonstrate the superiority of HEPES buffer in the absence of magnesium or both calcium and magnesium after 3 days of storage.

The foregoing invention has been described in some detail for purposes of clarity and understanding. It will be clear to one skilled in the art from a reading of the present disclosure that various changes can be made in form and detail without departing from the true scope of the invention.

What is claimed is:

1. A method of maintaining viability of a cell, tissue or organ comprising:
   (i) contacting said cell, tissue or organ with a solution comprising transferrin and selenium; and
   (ii) maintaining said cell, tissue or organ in contact with said solution at a temperature of about 4° C. or less in a non-frozen state.

2. The method according to claim 1 wherein transferrin is present in said solution at a concentration in the range of 2.5 μg/ml to 10 μg/ml.

3. The method according to claim 2 wherein transferrin is present in said solution at a concentration of about 5 μg/ml.

4. The method according to claim 1 wherein selenium is present in said solution at a concentration in the range of 2.5 ng/ml to 7.5 ng/ml.

5. The method according to claim 4 wherein selenium is present in said solution at a concentration of about 5.0 ng/ml.

6. The method according to claim 1 wherein said solution further comprises insulin.

7. The method according to claim 6 wherein insulin is present in said solution at a concentration in the range of 2.5 μg/ml to 7.5 μg/ml.

8. The method according to claim 7 wherein insulin is present in said solution at a concentration of about 5 μg/ml.

9. The method according to claim 1 wherein said solution further comprises hydrocortisone.

10. The method according to claim 9 wherein hydrocortisone is present in said solution at a concentration in the range of 25 ng/ml to 40 ng/ml.

11. The method according to claim 10 wherein hydrocortisone is present in said solution at a concentration of about 36 ng/ml.

12. A cell, tissue or organ storage solution comprising insulin, transferrin, hydrocortisone, selenium and 4-(2-hydroxyethyl)-1-piperazineethanesulfonic acid.

13. The storage solution according to claim 12 wherein insulin, transferrin, hydrocortisone, selenium and 4-(2-hydroxyethyl)-1-piperazineethanesulfonic acid are present in said solution at concentrations in the ranges of 2.5 μg/ml to 7.5 μg/ml, 2.5 μg/ml to 10 μg/ml, 25 ng/ml to 40 ng/ml, 2.5 ng/ml to 7.5 ng/ml and 2.95 g/l to 8.85 g/l, respectively.

14. The storage solution according to claim 13 wherein insulin, transferrin, hydrocortisone, selenium and 4-(2-hydroxyethyl)-1-piperazineethanesulfonic acid are present in said solution at concentrations of about 5 μg/ml, about 5 μg/ml, about 36 ng/ml, about 5 ng/ml, and about 4.425 g/l, respectively.

* * * * *